United States Patent [19]
Umemoto et al.

[11] Patent Number: 4,873,373
[45] Date of Patent: Oct. 10, 1989

[54] PROCESS FOR PREPARATION OF 3-PHENOXYBENZYL 2-(4-ALKOXYPHENYL)-2-METHYLPROPYL ETHERS

[75] Inventors: Mitsumasa Umemoto; Tamotsu Asano; Hironobu Horie; Akinobu Takagi; Nobuyasu Tamura; Takeshi Nishida, all of Fukuoka, Japan

[73] Assignee: Mitsui Toatsu Chemicals, Inc., Tokyo, Japan

[21] Appl. No.: 890,143
[22] PCT Filed: Apr. 18, 1986
[86] PCT No.: PCT/JP86/00198
§ 371 Date: Jul. 16, 1986
§ 102(e) Date: Jul. 16, 1986
[87] PCT Pub. No.: WO86/06367
PCT Pub. Date: Nov. 6, 1986

[30] Foreign Application Priority Data

Apr. 19, 1985 [JP] Japan .................................. 60-82661

[51] Int. Cl.$^4$ .............................................. C07C 41/24
[52] U.S. Cl. ...................................... 568/637; 568/636
[58] Field of Search ................. 568/636, 637; 252/373

[56] References Cited

U.S. PATENT DOCUMENTS 4,510,071  4/1985  Joyner et al. ....................... 252/373
4,542,243  9/1985  Umemoto et al. .................. 568/655

FOREIGN PATENT DOCUMENTS 2131424  6/1984  United Kingdom .

OTHER PUBLICATIONS

Okamoto et al, "The Transition–Metal Catalyzed Dehalogenation of Aromatic Halides by NaOH–Alcohols. A Facile Method of Destroying Aromatic Polyhalides", *Bull. of the Chem. Soc. of Jpn.*, vol. 54, No. 4, 1981.

*Primary Examiner*—Bruce Gray
*Attorney, Agent, or Firm*—Browdy and Neimark

[57] ABSTRACT

Disclosed is a process for preparing 3-phenoxybenzyl 2-(4-alkoxyphenyl)-2-methylpropyl ethers represented by the following formula (I):

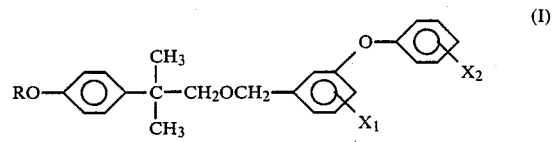

wherein R stands for a lower alkyl group, and $X_1$ and $X_2$ stand for a hydrogen atom or fluorine atom, which comprises subjecting a 3-phenoxybenzyl 2-(4-alkoxy-3-halogenophenyl)-2-methylpropyl ether or 3-phenoxybenzyl-2-(4-alkoxy-3,5-dihalogenophenyl)-2-methylpropyl ether represented by the following formula (II):

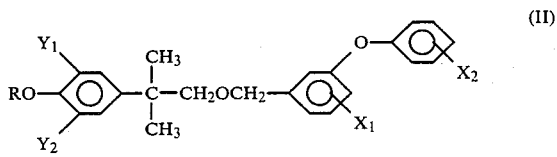

wherein R stands for a lower alkyl group, $X_1$ and $X_2$ stand for a hydrogen atom or fluorine atom, and $Y_1$ and $Y_2$ stand for a hydrogen atom, chlorine atom, bromine atom or iodine atom, with the proviso that at least one of $Y_1$ and $Y_2$ is a chlorine atom, bromine atom or iodine atom, to dechlorination, debromination or deiodination by hydrogenation, wherein the dechlorination, debromination or deiodination is carried out in the presence of a hydrogenation catalyst by using as a hydrogenative reducing agent a lower aliphatic alcohol and an alkali compound selected from the group comprising alkali metal hydroxides and alkaline earth metal hydroxides.

According to this process, compounds of the formula (I) can be obtained in high yields with safety without using hydrogen.

7 Claims, No Drawings

PROCESS FOR PREPARATION OF 3-PHENOXYBENZYL 2-(4-ALKOXYPHENYL)-2-METHYLPROPYL ETHERS

FIELD OF INDUSTRIAL APPLICATION

The present invention relates to a process for the preparation of 3-phenoxybenzyl 2-(4-alkoxyphenyl)-2-methylpropyl ethers represented by the following formula (I):

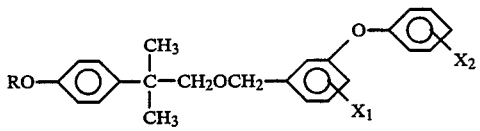

wherein R stands for a lower alkyl group, and $X_1$ and $X_2$ stand for a hydrogen atom or fluorine atom.

A 3-phenoxybenzyl ether type derivative represented by the formula (I) is an excellent pest-controlling agent having very high insecticidal and acaricidal activities, being excellent in the immediate effect and residual effect and being less toxic to not only men and domestic animals but also fish.

PRIOR ART

A process for the preparation of a compound of the formula (I) having an alkoxy group on the benzene nucleus of the neophyl group is disclosed in Japanese Patent Application Laid-Open Specification No. 154427/81, and it is taught that the neophyl derivative can be prepared by condensing a compound represented by the following formula (III):

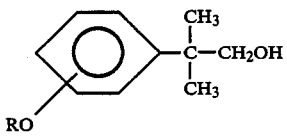

with a 3-phenoxybenzyl halide or alcohol or by condensing a compound represented by the following formula (IV):

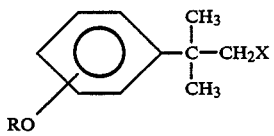

wherein X stands for a halogen atom,
with a 3-phenoxybenzyl alcohol.

The reaction path for the synthesis of the compound of the formula (III) is long, and the process for preparing the compound of the formula (I) from the compound of the formula (III) as the starting material is disadvantageous from the industrial viewpoint.

As the process for preparing the compound of the formula (IV), for example, the above-mentioned laid-open specification discloses a process represented by the following reaction formulas:

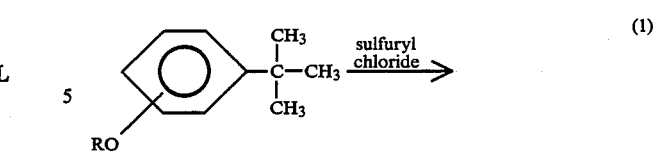

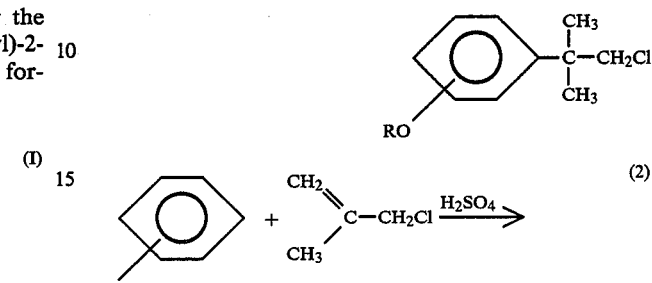

However, in the case where the 4-position is substituted with a lower alkoxy group, according to the process of the reaction formula (1), a nuclear chlorination reaction is preferentially advanced, and the intended 4-alkoxyneophyl chloride is in only a very poor yield obtained. Furthermore, according to the process of the reaction formula (2), an alkylation reaction at the ortho-position to the alkoxy group is preferentially advanced and a large quantity of an ortho-isomer is formed as a by-product, and since effective separation of the isomers is difficult, the intended 4-alkoxyneophyl chloride having a high purity can be obtained only in a very low yield.

Moreover, the obtained 4-alkoxyneophyl chloride is an unstable compound, and storage and handling thereof on an industrial scale involve various difficulties.

As the improved process for overcoming the foregoing disadvantages, Japanese Patent Application Laid-Open Specification No. 73535/84 proposes a process in which a 4-alkoxyhalogenoneophyl halide having at least one chlorine or bromine atom substituted at the ortho-position to the alkoxy group is used and this compound is reacted with a 3-phenoxybenzyl alcohol to obtain a compound of the formula (II) and a compound of the formula (I) is obtained from this compound of the formula (II).

In this laid-open specification, it is taught that the compound of the formula (I) is obtained by subjecting the compound of the formula (II) to catalytic hydrodehalogenation using hydrogen in a solvent such as methanol in the presence of a hydrogenation catalyst such as palladium and a base as the dehydrohalogenating agent.

The fatal defect of this process is that hydrogen gas is used at the dehalogenating step. Namely, in the case where this process is worked on an industrial scale, special care should be taken to maintain safety and the location is limited because hydrogen gas-supplying equipment is necessary. Moreover, large equipment expenses are necessary and hence the process is disadvantageous also from the economical viewpoint.

In the catalytic hydrogenation reaction using hydrogen, cleaving is readily caused in a compound having an O-benzyl group and a fluorine atom, such as the compound of the formula (II), unless the hydrogenation conditions are strictly controlled. It has been found that this tendency is especially prominent when a palladium type catalyst, which is known to be preferred as a dehalogenation catalyst, is used.

As the process not using hydrogen, there may be considered a process in which a known reducing agent such as sodium formate is used. However, it has been found that even if the compound of the formula (II) used in the present invention is reacted with sodium formate as the reducing agent, the unreacted substance and the by-product formed by cleaving of the ether linkage are contained in large quantities in the dehalogenation reaction liquid.

MEANS FOR SOLVING THE PROBLEMS

We made research on the process for obtaining the compound of the formula (I) by removing chlorine, bromine or iodine from the compound of the formula (II) by hydrodehalogenation reaction, and as the result, it ws found that if an alkali compound and an alcohol are present in amounts larger than the stoichiometrically necessary amounts in the presence of a hydrogenation catalyst, hydrogen gas need not indispensably be added to the reaction and the reaction can be advanced only by hydrogen generated from the alkali and alcohol, and to our great surprise it also was found that the dechlorination or debromination reaction can be carried out in a yield comparable to or higher than the yield attained in the process using hydrogen gas supplied from outside of the reaction system, disclosed in the above-mentioned laid-open specification. We have now completed the present invention based on these findings.

Since hydrogen gas supplied from outside of the system is not used, the process of the present invention is much safer and is advantageous from the economical viewpoint over the process using hydrogen gas supplied from outside of the reaction system. By dint of this advantage and high functional utility of compounds prepared according to the process of the present invention, the process of the present invention has a very high industrial value.

In the hydrodehalogenative reduction reaction of the present invention, in order to obtain the intended compound of the formula (1) in a high yield without using hydrogen supplied from outside of the reaction system, an alkali metal or alkaline earth metal hydroxide and a lower aliphatic alcohol should be used in combination besides a hydrogenation catalyst and a customarily used dehydrohalogenating agent such as a base. The reason is presumed to be as follows.

For example, when sodium hydroxide is used as the alkali metal hydroxide and methanol is used as the lower aliphatic alcohol, sodium hydroxide is reacted with methanol in the presence of a hydrogenation catalyst to form formic acid and this formic acid is decomposed to sodium formate and finally to sodium carbonate. At this time, stoichiometrically speaking, by using 2 moles of sodium hydroxide per mole of methanol, 3 moles of hydrogen is finally formed, and this hydrogen acts efficiently on the dehalogenation reaction of the compound of the formula (II) under the influence of the catalyst.

Accordingly, in the process of the present invention, an alkali compound for generating hydrogen should be present in addition to a base acting as the dehydrohalogenating agent. As the alkali compound, there can be mentioned, for example, sodium hydroxide, potassium hydroxide and calcium hydroxide.

The alkali compound may be used singly in a large amount so that it also acts as the dehydrohalogenating agent, but, of course, a different base may be used as the dehydrohalogenating agent in combination with the alkali compound.

As the base that can be used as the dehydrohalogenating agent in combination with the alkali compound, there can be mentioned inorganic and organic bases such as potassium carbonate, sodium carbonate and, and aliphatic, aromatic and heterocyclic amines such as triethylamine, ethylenediamine, diethylaniline and pyridine. Single use of an inorganic base is preferred, and single use of an alkali metal hydroxide, particularly sodium hydroxide, is especially advantageous from the economical viewpoint.

In the present invention, when the alkali metal hydroxide alone is used, hydrogen is generated by reacting the alkali in an amount of at least two moles with the stoichiometric amount of methanol, and consequently the alkali should be used in an amount of at least 0.6 mole of the stoichiometric amount per mole of the starting compound of the formula (II), for example, a 3-phenoxybenzyl-2-(4-alkoxy-3-halogenophenyl)-2-methylpropyl ether.

When the action of the alkali as the dehydrohalogenating agent is also intended, it is preferred that the alkali be used in an amount of 1.0 to 10 moles per mole of the compound of the formula (II), for example, a 3-phenoxybenzyl 2-(4-alkoxy-3-halgenophenyl)-2-methylpropyl ether.

As the alcohol used as the reducing agent in combination with the alkali in the process of the present invention, there can be mentioned lower aliphatic monools and diols such as methanol, ethanol, isopropanol, n-propanol, n-butanol, isobutanol, ethylene glycol and propylene glycol. Monools, especially methanol, are preferred. These alcohols may be used in the form of mixtures of two or more of them. When an alkali metal hydroxide is used as the alkali and a monool is used as the alcohol, it is necessary that the alcohol should be used in an amount of at least about 0.3 mole of the stoichiometric amount, preferably 0.4 to 30 moles, per mole of the compound of the formula (II), for example, a 3-phenoxybenzyl 2-(4-alkoxy-3-halogenophenyl)-2-methylpropyl ether, and when the alcohol is used also as the reaction medium described below, the amount of the alcohol is appropriately selected while taking the amount of the alcohol used as the reaction medium into consideration.

In the hydrodehalogenation step, addition of water is not absolutely necessary. However, in order to increase the reaction rate, it is preferred that water be added and the reaction be carried out in a water-containing organic solvent. Various organic solvents, for example, alcohols such as methanol, polyhydric alcohols such as ethylene glycol, acetic acid and acetic acid esters may be used as the organic solvent. However, it is preferred that the same alcohol as used in the reducing reaction be used. When the organic solvent is used, it is preferred that the concentration be adjusted to 20 to 80%. When an alcohol and water are used as the reaction medium, the concentration of the alcohol is selected within the above-mentioned range while taking the amount of the alcohol used in the reducing reaction into consideration.

The amount of the reaction medium used can be selected within a broad range, but in view of the reaction rate and the volume efficiency of the reaction vessel, it is preferred that the reaction medium be used in an amount of 2 to 10 parts by volume per part by volume of the compound of the formula (II).

As the catalyst, there can be used a nickel catalyst such as Raney nickel, a palladium catalyst such as palladium-carbon or palladium-alumina, and a platinum catalyst. Palladium-carbon is especially advantageous. The catalyst is used in an amount of 0.1 to 20% by weight, preferably 1 to 6% by weight, based on the compound represented by the formula (II).

As the 4-alkoxyneophyl ether derivative of the formula (I) prepared according to the process of the present invention, there can be mentioned 3-phenoxybenzyl 2-(4-methoxyphenyl)-2-methylpropyl ether, 3-phenoxy-4-fluorobenzyl 2-(4-methoxyphenyl)-2-methylpropyl ether, 3-(4-fluorophenoxy)benzyl 2-(4-methoxyphenyl)-2-methylpropyl ether, 3-(4-fluorophenoxy)-4-fluorobenzyl 2-(4-methoxyphenyl)-2-methylpropyl ether, 3-phenoxybenzyl 2-(4-ethoxyphenyl)-2-methylpropyl ether, 3-phenoxy-4-fluorobenzyl 2-(4-ethoxyphenyl)-2-methylpropyl ether, 3-(4-fluorophenoxy)benzyl 2-(4-ethoxyphenyl)-2-methylpropyl ether, 3-(4-fluorophenoxy)-4-fluorobenzyl 2-(4-ethoxyphenyl)-2-methylpropyl ether, 3-phenoxy-6-fluorobenzyl 2-(4-ethoxyphenyl)-2-methylpropyl ether, 3-(2-fluorophenoxy)benzyl 2-(4-ethoxyphenyl)-2-methylpropyl ether, 3-phenoxybenzyl 2-(4-(i-propoxy)phenyl)-2-methylpropyl ether, 3-phenoxy-4-fluorobenzyl 2-(4-(i-propoxy)phenyl-2-methylpropyl ether, 3-phenoxybenzyl 2-(4-(1-methylpropoxy)phenyl)-2-methylpropyl ether, 3-phenoxybenzyl 2-(4-(n-butoxy)phenyl)-2-methylpropyl ether, 3-phenoxybenzyl 2-(4-(t-butoxy)phenyl)-2-methylpropyl ether and 3-phenoxybenzyl 2-(4-(n-pentyloxy)phenyl)-2-methylpropyl ether.

A general embodiment of the present invention will now be described. The dehalogenation reaction of the present invention may be carried out under atmospheric pressure according to the amounts of the hydrogenation catalyst, the alkali compound and the lower alcohol used. However, it is generally preferred that the reaction be carried out under an elevated pressure.

A reaction vessel is charged with predetermined amounts of a 3-phenoxybenzyl 2-(4-alkoxy-3-halogenophenyl)-2-methylpropyl ether or 3-phenoxybenzyl 2-(4-alkoxy-3,5-dihalogenophenyl)-2-methylpropyl ether represented by the general formula (II), an alcohol and alkali as the reducing agent and a hydrogenation catalyst, and the mixture is heated at 50° to 220° C., preferably 80° to 150° C., and stirred at this temperature for 0.5 to 50 hours, preferably 3 to 30 hours. The reaction mixture is cooled to room temperature, and if necessary, in order to form a homogeneous solution, a nonpolar solvent such as water or benzene is added, and the catalyst is separated by filtration under reduced pressure. The mother liquor is subjected to phase separation, and the oil layer is washed with water and dehydrated and the solvent is removed to give a 3-phenoxybenzyl 2-(4-alkoxyphenyl)-2-methylpropyl ether represented by the general formula (I) as the intended product.

The obtained product can be satisfactorily used as such as an insecticidal and acaricidal agent, but according to need, the product may be purified by reduced pressure distillation, column chromatography or recrystallization.

The present invention will now be described in detail more with reference to the following examples.

EXAMPLE 1

An autoclave having a capacity of 500 ml was charged with 60.0 g (0.146 mole) of 3-phenoxybenzyl 2-(3-chloro-4-ethoxyphenyl)-2-methylpropyl ether, 18.8 g (0.47 mole) of flaky sodium hydroxide, 2.4 g of 5%-palladium-carbon (50% wet), 85.3 g (2.66 moles) of methanol and 36 g of water. The autoclave was sealed and the inner atmosphere was replaced by nitrogen, and the mixture was heated with stirring at an inner temperature of 110° C. for 12 hours to complete reaction.

The reaction mixture was cooled to 50° C. and the residual pressure was released, and 100 ml of benzene was added into the autoclave to dissolve the oil layer. Then, the catalyst was removed by filtration, and the filtrate was allowed to stand still to cause phase separation, and the benzene layer was recovered and washed with 120 ml of water three times, and benzene was removed by distillation under reduced pressure to give an oily product. From the results of the analysis of the oily product by gas chromatography according to the internal standard method, it was found that the oily product comprised 98.8% of 3-phenoxybenzyl 2-(4-ethoxyphenyl)-2-methylpropyl ether and 0.3% of unreacted starting 3-phenoxybenzyl 2-(3-chloro-4-ethoxyphenyl)-2-methylpropyl ether, and that the content of each of 3-phenoxytoluene and 4-ethoxyneophyl alcohol formed by cleaving of the ether linkage was lower than 0.3%. The amount of the obtained oily product was 53.8 g, and the yield was 96.7%.

EXAMPLE 2

An autoclave having a capacity of 300 ml was charged with 60.0 g (0.140 mole) of 3-phenoxy-4-fluorobenzyl 2-(3-chloro-4-ethoxyphenyl)-2-methylpropyl ether, 18.8 g (0.47 mole) of flaky sodium hydroxide, 2.4 g of 5%-palladium-carbon (50% wet), 56.9 g (1.77 moles) of methanol and 54.0 g of water. The autoclave was sealed and the inner atmosphere was replaced by nitrogen, and the mixture was heated with stirring at an inner temperature of 120° C. for 10 hours to complete reaction.

The reaction mixture was cooled to room temperature and the residual pressure was released, and 100 ml of benzene was added into the autoclave to dissolve the oily portion. Then, the catalyst was removed by filtration, and the filtrate was sufficiently shaken and allowed to stand still to cause phase separation. Then, the obtained benzene layer was washed with 100 ml of water three times and benzene was removed by distillation under reduced pressure to give an oily product. From the results of the analysis of the oily product by gas chromatography according to the internal standard method, it was found that the oily product comprised 98.2% of 3-phenoxy-4-fluorobenzyl 2-(4-ethoxyphenyl)-2-methylpropyl ether and 0.7% of starting 3-phenoxy-4-fluorobenzyl 2-(3-chloro-4-ethoxyphenyl)-2-methylpropyl ether, and that the content of each of 3-phenoxy-4-fluorotoluene and 4-ethoxyneophyl alcohol formed by cleaving of the ether linkage was lower than 0.2%. Moreover, 0.8% of 3-phenoxybenzyl 2-(4-ethoxyphenyl)-2-methylpropyl ether presumed to have been formed by reduction of the fluorine atom was contained.

The amount of the obtained oily product was 54.0 g and the yield was 96.0%.

EXAMPLE 3

A four-necked glass flask having a capacity of 300 ml was charged with 60.0 g (0.146 mole) of 3-phenoxybenzyl 2-(3-chloro-4-ethoxyphenyl)-2-methylpropyl ether, 18.8 g (0.47 mole) of flaky sodium hydroxide, 4.8 g of 5%-palladium-carbon (50% wet), 86.2 g (1.87 moles) of ethanol and 36 g of water, and the mixture was heated with stirring at the boiling point (81° C.) for 6 hours to complete reaction.

The reaction mixture was cooled to 50° C., and 50 ml of benzene was added into the reaction vessel to dissolve the oily portion. The catalyst was removed by filtration and the filtrate was allowed to stand still to cause phase separation. The benzene layer was recovered and washed with 100 ml of water three times. Benzene was removed by distillation under reduced pressure to give an oily product.

From the results of the analysis of the oily product gas chromatography according to the internal standard method, it was found that the oily product comprised 96.2% of 3-phenoxybenzyl 2-(4-ethoxyphenyl)-2-methylpropyl ether and 1.5% of unreacted starting 3-phenoxybenzyl 2-(3-chloro-4-ethoxyphenyl)-2-methylpropyl ether, and that the oily product contained 0.5% of 3-phenoxytoluene and 0.2% of 4-ethoxyneophyl alcohol, each being formed by cleaving of the ether linkage. The amount of the obtained oily product was 54.0 g and the yield was 94.5%.

EXAMPLE 4

A four-necked glass flask having a capacity of 300 ml was charged with 60.0 g (0.146 mole) of 3-phenoxybenzyl 2-(3-chloro-4-ethoxyphenyl)-2-methylpropyl ether, 23.5 g (0.588 mole) of flaky sodium hydroxide, 4.8 g of 5%-palladium-carbon (50% wet), 18 g (0.290 mole) of ethylene glycol and 144 g of water, and the mixture was heated with stirring at the boiling point (104° C.) for 12 hours to complete reaction.

The reaction mixture was cooled to 50° C. and 50 ml of benzene was added into the reaction vessel to dissolve the oily portion. The catalyst was removed by filtration and the filtrate was allowed to stand still to cause phase separation. The benzene layer was washed with 100 ml of water three times. Benzene was removed by distillation under reduced pressure to give an oily product.

From the results of the analysis of the oily product gas chromatography according to the internal standard method, it was found that the oily product comprised 95.3% of 3-phenoxybenzyl 2-(4-ethoxyphenyl)-2-methylpropyl ether and 2.2% of unreacted starting 3-phenoxybenzyl 2-(3-chloro-4-ethoxyphenyl)-2-methylpropyl ether, and that the oily product contained 0.6% of 3-phenoxytoluene and 0.4% of 4-ethoxyneophyl alcohol, each being formed by cleaving of the ether linkage. The amount of the obtained oily product was 54.3 g and the yield was 94.1%.

REFERENTIAL EXAMPLE

An autoclave having a capacity of 500 ml was charged with 60.0 g (0.146 mole) of 3-phenoxybenzyl 2-(3-chloro-4-ethoxyphenyl)-2-methylpropyl ether, 7.5 g (0.188 mole) of flaky sodium hydroxide, 7.2 g of 5%-palladium-carbon (50% wet), 83.5 g of methanol and 36 ml of water, and the autoclave was sealed and the inner atmosphere was replaced by nitrogen. Hydrogen was filled in the autoclave so that the pressure was 8 kg/cm$^2$G. The mixture was heated with stirring at an inner temperature of 110° C. for 12 hours while supplying hydrogen so that the pressure was 8 to 10 kg/cm$^2$G, to complete reaction.

The reaction mixture was cooled to room temperature and the residual pressure was released, and 120 ml of benzene was added into the autoclave to dissolve the oil layer. Then, the insoluble substance was removed by filtration, and the mother liquid was washed with 30 ml of benzene, sufficiently shaken and allowed to stand still to cause phase separation and give a benzene layer. The benzene layer was washed with 120 ml of water three times and benzene was removed by distillation under reduced pressure to give an oily product. From the results of the analysis of the oily product by gas chromatography according to the internal standard method, it was found that the oily product comprised 98.5% of 3-phenoxybenzyl 2-(4-ethoxyphenyl)-2-methylpropyl ether and 0.5% of unreacted starting 3-phenoxybenzyl 2-(3-chloro-4-ethoxyphenyl)-2-methylpropyl ether, and that the content of each of 3-phenoxytoluene and 4-ethoxyneophyl alcohol formed by cleaving of the ether linkage was lower than 0.3%. The amount of the obtained oily product was 53.6 g and the yield was 96.0%.

EXAMPLE 5

An autoclave having a capacity of 300 ml was charged with 30.0 g (0.066 mole) of 3-phenoxybenzyl 2-(3-bromo-4-ethoxyphenyl)-2-methylpropyl ether, 8.5 g of flaky sodium hydroxide, 0.9 g of 5%-palladium-carbon (50% wet), 42.7 g (2.3 moles) of methanol and 18 g of water, and the autoclave was sealed and the inner atmosphere was replaced by nitrogen. The mixture was heated with stirring at an inner temperature of 110° C. for 10 hours to complete reaction.

The reaction mixture was cooled to 50° C. and the residual pressure was released, and 70 ml of benzene was added into the autoclave to dissolve the oil layer. The catalyst was removed by filtration, and the filtrate was allowed to stand still to cause phase separation to give a benzene layer. Then, the benzene layer was washed with 100 ml of water three times, and benzene was removed by distillation under reduced pressure to give an oily product. From the results of the analysis of oil product by gas chromatography according to the internal standard method, it was found that the oily product comprised 98.6% of 3-phenoxybenzyl 2-(4-ethoxyphenyl)-2-methylpropyl ether and 0.4% of unreacted starting 3-phenoxybenzyl 2-(3-bromo-4-ethoxyphenyl)-2-methylpropyl ether, and that the content of each of 3-phenoxytoluene and 4-ethoxyneophyl alcohol formed by cleaving of the ether linkage was lower than 0.3%. The amount of the obtained oily product was 23.8 g and the yield was 94.4%.

EXAMPLE 6

An autoclave having a capacity of 300 ml was charged with 40.0 g (0.072 mole) of 3-phenoxybenzyl 2-(3-iodo-4-ethoxyphenyl)-2-methylpropyl ether, 9.3 g (0.23 mole) of flaky sodium hydroxide, 1.2 g of 5%-palladium-carbon (50% wet), 64.0 g (2.0 moles) of methanol and 27 g of water, and the autoclave was sealed and the inner atmosphere was replaced by nitrogen. The mixture was heated with stirring at an inner temperature of 110° C. for 10 hours to complete reaction.

An oily product was obtained by carrying out the post-treatment in the same manner as in Example 5. From the results of the analysis of the oily product by gas chromatography according to the internal standard method, it was found that the oily product comprised 99.2% of 3-phenoxybenzyl 2-(4-ethoxyphenyl)-2-methylpropyl ether and 0.1% of unreacted starting 3-phenoxybenzyl 2-(3-iodo-4-ethoxyphenyl)-2-methylpropyl ether, and that the content of each of 3-phenoxytoluene and 4-ethoxyneophyl alcohol formed by cleaving of the ether linkage was lower than 0.3%. The amount of the obtained oily product was 26.0 g and the yield was 95.1%.

EXAMPLE 7

The dechlorination reaction was carried out in the same manner as in Example 1 except that 1.44 g of 10%-palladium-alumina (100% dry) was used instead of the 5%-palladium-carbon used as the hydrogenation catalyst in Example 1, and an oily product was obtained by carrying out the post-treatment in the same manner as in Example 1. From the results of the analysis of the oily product by gas chromatography according to the internal standard method, it was found that the oily product comprised 97.4% of 3-phenoxybenzyl 2-(4-ethoxyphenyl)-2-methylpropyl ether and 0.5% of unreacted starting 3-phenoxybenzyl 2-(3-chloro-4-ethoxyphenyl)-2-methylpropyl ether, and that the content of each of 3-phenoxytoluene and 4-ethoxyneophyl alcohol formed by cleaving of the ether linkage was lower than 0.7%. The amount of the obtained oily product was 52.0 g and the yield was 93.2%.

COMPARATIVE EXAMPLE

An autoclave having a capacity of 300 ml was charged with 60.0 g (0.145 mole) of 3-phenoxybenzyl 2-(3-chloro-4-ethoxyphenyl)-2-methylpropyl ether, 29.8 g (0.438 mole) of sodium formate, 4.8 g of 5%-palladium-carbon (50% wet) and 144 ml of water, and the mixture was heated with stirring at an inner temperature of 110° C. for 12 hours to complete reaction.

The reaction mixture was cooled to room temperature, and 100 ml of benzene was added into the reaction vessel to dissolve the oily portion. Then, the catalyst was removed by filtration and the filtrate was allowed to stand still to cause phase separation to obtain a benzene layer. Then benzene layer was washed with 100 ml of water three times, and benzene was removed by distillation under reduced pressure to give an oily product. From the results of the analysis of the oily product by gas chromatography according to the internal standard method, it was found that the oily product comprised 65.8% of 3-phenoxybenzyl 2-(4-ethoxyphenyl)-2-methylpropyl ether, 21.8% of unreacted starting 3-phenoxybenzyl 2-(3-chloro-4-ethoxyphenyl)-2-methylpropyl ether, and 4.4% of 3-phenoxytoluene and 2.9% of 4-ethoxyneophyl alcohol as by-products formed by cleaving of the ether linkage. The amount of the obtained oily product was 57.4 g and the yield was 68.7%.

What is claimed is:

1. A process for the preparation of 3-phenoxybenzyl 2-(4-alkoxyphenyl)-2-methylpropyl ethers represented by the following formula (I):

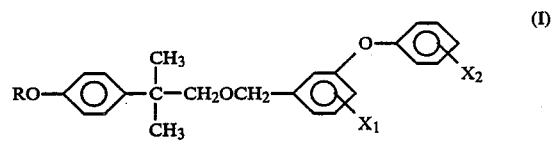

wherein R represents a lower alkyl group, and $X_1$ and $X_2$ represent a hydrogen atom or fluorine atom, which comprises subjecting a 3-phenoxybenzyl 2-(4-alkoxy-3-halogenophenyl)-2-methylpropyl ether or 3-phenoxybenzyl 2-(4-alkoxy-3,5-dihalogenophenyl)-2-methylpropyl ether represented by the following formula (II):

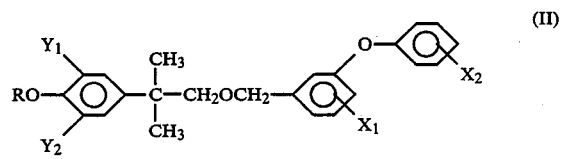

wherein R stands for a lower alkyl group, $X_1$ and $X_2$ represent a hydrogen atom or fluorine atom, and $Y_1$ and $Y_2$ represent a hydrogen atom, chlorine atom, bromine atom or iodine atom, with the proviso that at least one of $Y_1$ and $Y_2$ is a chlorine atom, bromine atom or iodine atom, to dechlorination, debromination or deiodination by hydrogenation in the presence of a dehydrohalogenating base in an amount of 1 to 10 moles per mole of the compound of formula (II), wherein the dechlorination, debromination or deiodination is carried out in the presence of a hydrogenation catalyst by using as a hydrogenative reducing agent a lower aliphatic alcohol in an amount of at least 0.3 mole of the stoichiometric amount per mole of the compound of formula (II) and an alkali compound selected from alkali metal hydroxides in an amount effective to form three moles of hydrogen for each mole of the lower aliphatic alcohol, said amount being at least 0.6 moles for each mole of the compound of formula (II), without introducing hydrogen from outside of the reaction system.

2. A process according to claim 1, wherein said alkali compound is sodium hydroxide.

3. A process according to claim 1, wherein both said dehydrohalogenating base and said alkalai compound are sodium hydroxide.

4. A process according to claim 1, wherein said lower aliphatic alcohol is methanol.

5. A process according to claim 1, wherein said hydrogenation catalyst is a palladium catalyst.

6. A process according to claim 5, wherein said catalyst is palladium-carbon or palladium-alumina.

7. A process according to claim 1, wherein said dechlorination, debromination or deiodination by hydrogenation is performed in the presence of an aqueous phase.

* * * * *